(12) United States Patent
Kitahara

(10) Patent No.: US 7,903,349 B2
(45) Date of Patent: Mar. 8, 2011

(54) IMAGING LENS AND IMAGING APPARATUS USING IMAGING LENS

(75) Inventor: Yu Kitahara, Saitama (JP)

(73) Assignee: Fujinon Corporation, Saitama-Shi (JP)

(*) Notice: Subject to any disclaimer, the term of this patent is extended or adjusted under 35 U.S.C. 154(b) by 0 days.

(21) Appl. No.: 12/580,843

(22) Filed: Oct. 16, 2009

(65) Prior Publication Data
US 2010/0103539 A1    Apr. 29, 2010

(30) Foreign Application Priority Data
Oct. 28, 2008    (JP) ................................ P2008-276247

(51) Int. Cl.
*G02B 9/06* (2006.01)
(52) U.S. Cl. ......................................... 359/794; 359/795
(58) Field of Classification Search .................. 359/794, 359/795, 770, 753, 692
See application file for complete search history.

(56) References Cited

U.S. PATENT DOCUMENTS
5,682,269 A  10/1997  Kimura et al.
6,285,516 B1 * 9/2001  Ori ................................ 359/770

FOREIGN PATENT DOCUMENTS
| JP | 3254239 B2 | 2/2002 |
| JP | 3478643 B2 | 12/2003 |
| JP | 3723637 B2 | 12/2005 |
| JP | 3964533 B2 | 8/2007 |

* cited by examiner

*Primary Examiner* — Alicia M Harrington
(74) *Attorney, Agent, or Firm* — Birch, Stewart, Kolasch & Birch, LLP

(57) ABSTRACT

An imaging lens includes, in order from an object side, a first lens group having a positive power, an aperture diaphragm, and a second lens group having a positive or negative power. The first lens group includes, in order from the object side, a first lens which is a biconcave lens, a second lens that has a positive power and includes a convex image-side surface, and a third lens that has a positive power and includes a convex object-side surface. The second lens group includes, in order from the object side, a fourth lens that has a negative power and includes a concave image-side surface, and a fifth lens which is a biconvex lens. Each of the first to fifth lenses is a single spherical glass lens.

7 Claims, 10 Drawing Sheets

EXAMPLE 2

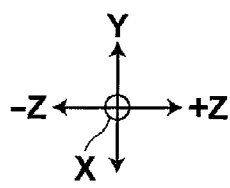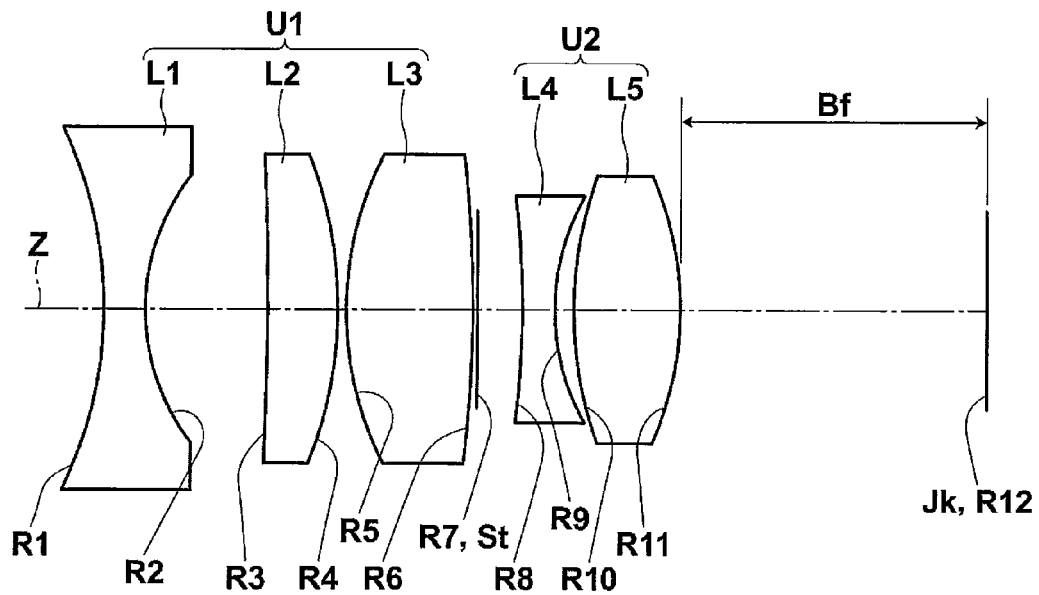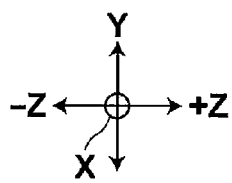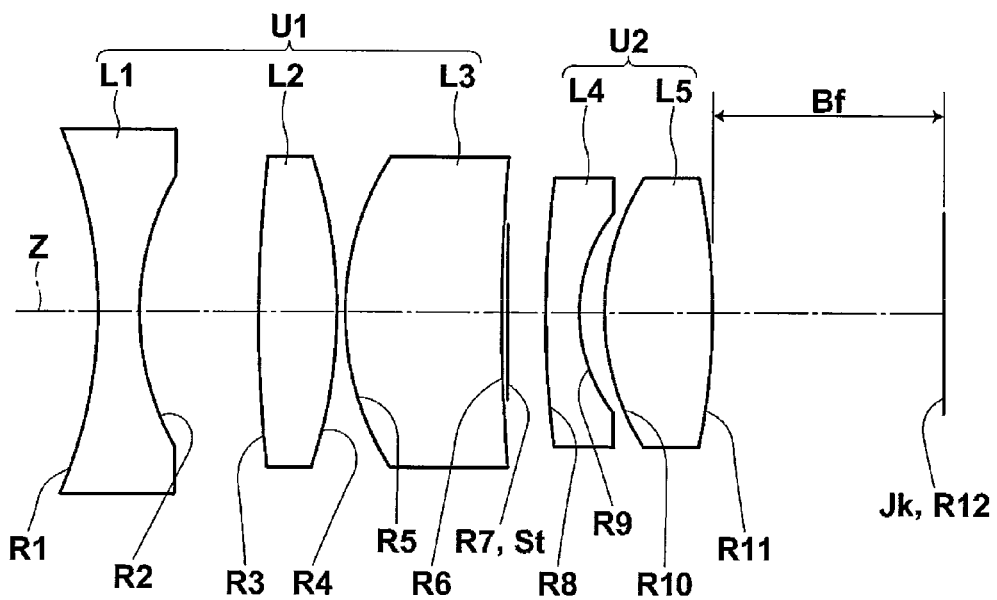

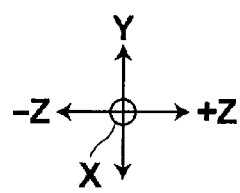
FIG.4
EXAMPLE 3
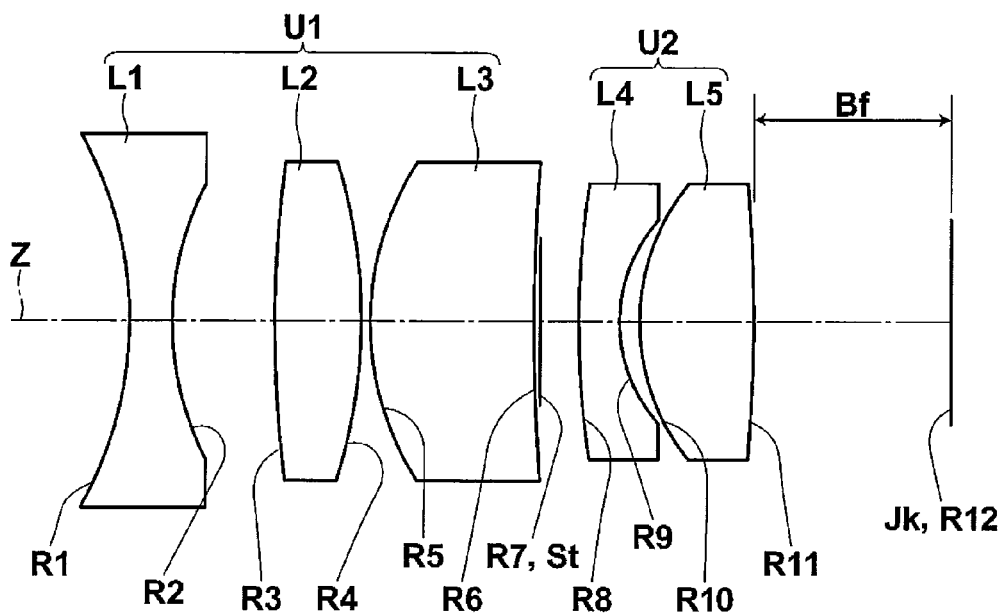
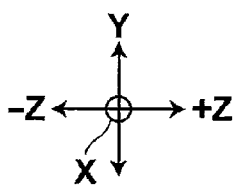
FIG.5
EXAMPLE 4
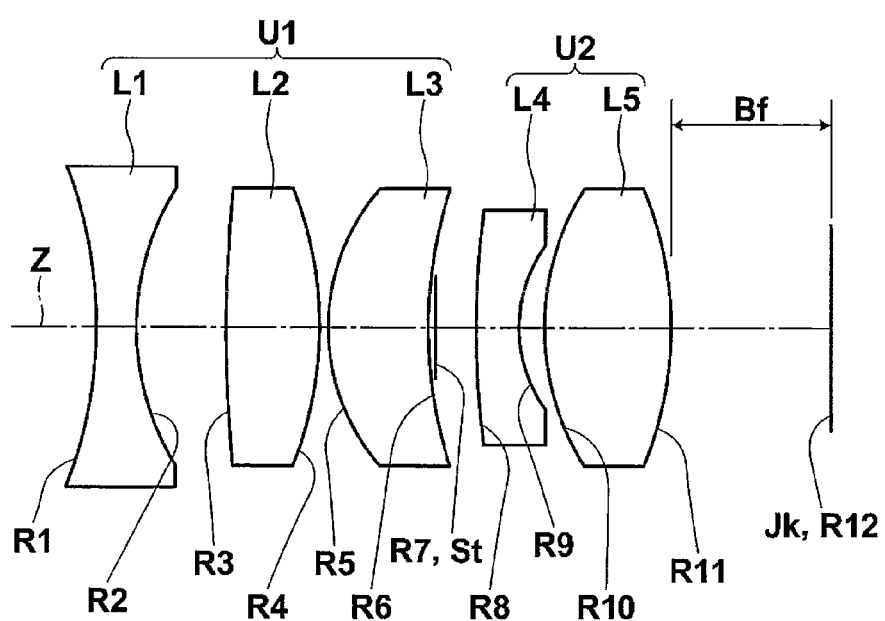

EXAMPLE 5

EXAMPLE 6

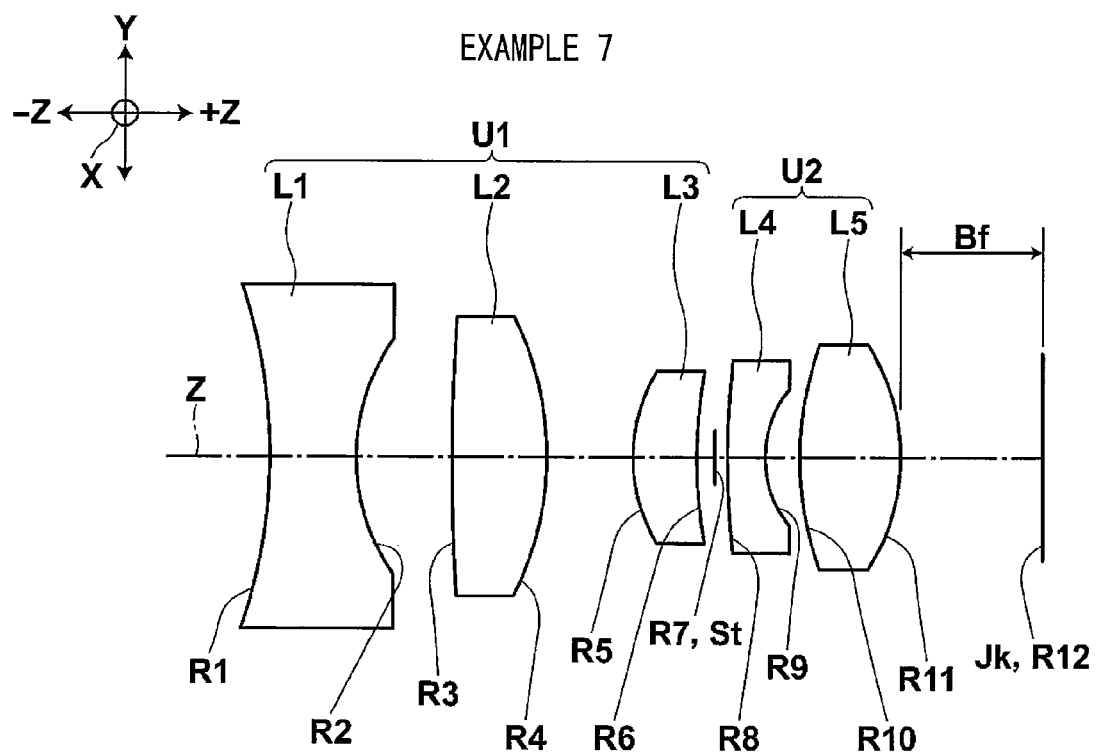

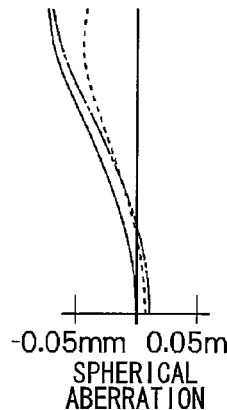

FIG.9A
EXAMPLE 1

Fno. = 2.00

-0.05mm  0.05mm
SPHERICAL
ABERRATION
—— e-LINE
----- g-LINE
——- C-LINE

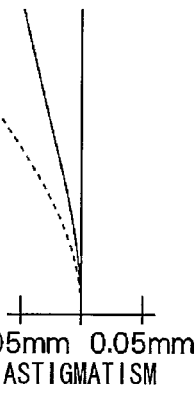

FIG.9B
EXAMPLE 1

ω=21.4°

-0.05mm  0.05mm
ASTIGMATISM

—— SAGITTAL
----- TANGENTIAL

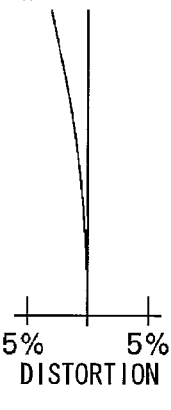

FIG.9C
EXAMPLE 1

ω=21.4°

-5%    5%
DISTORTION

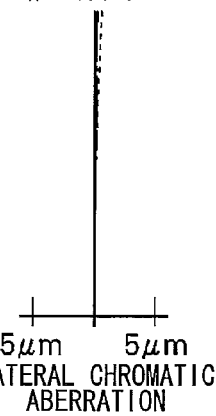

FIG.9D
EXAMPLE 1

ω=21.4°

-5μm    5μm
LATERAL CHROMATIC
ABERRATION
----- g-LINE
——- C-LINE

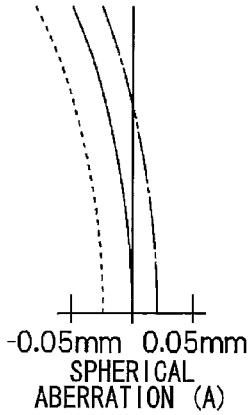

FIG.10A
EXAMPLE 2

Fno. = 2.00

-0.05mm  0.05mm
SPHERICAL
ABERRATION (A)
—— e-LINE
----- g-LINE
——- C-LINE

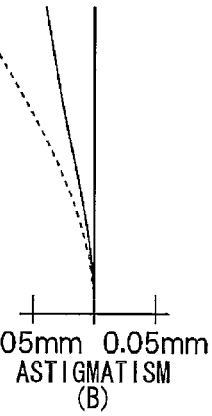

FIG.10B
EXAMPLE 2

ω=21.3°

-0.05mm  0.05mm
ASTIGMATISM
(B)
—— SAGITTAL
----- TANGENTIAL

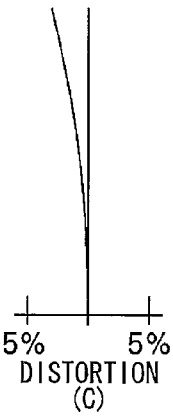

FIG.10C
EXAMPLE 2

ω=21.3°

-5%    5%
DISTORTION
(C)

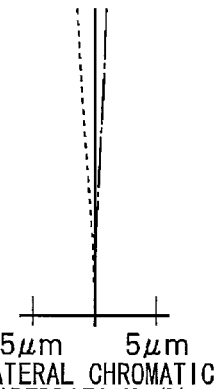

FIG.10D
EXAMPLE 2

ω=21.3°

-5μm    5μm
LATERAL CHROMATIC
ABERRATION (D)
----- g-LINE
——- C-LINE

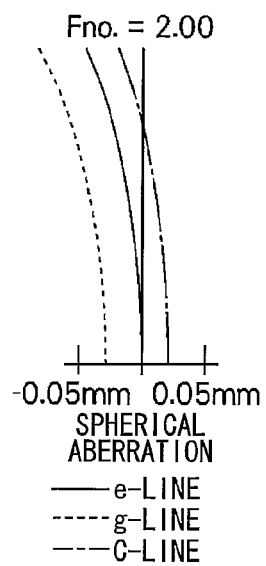

FIG.11A
EXAMPLE 3
Fno. = 2.00

-0.05mm  0.05mm
SPHERICAL
ABERRATION
——— e-LINE
----- g-LINE
——— C-LINE

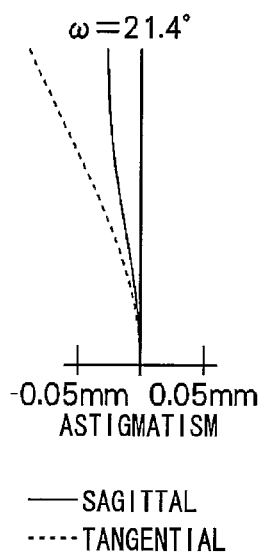

FIG.11B
EXAMPLE 3
ω=21.4°

-0.05mm  0.05mm
ASTIGMATISM
——— SAGITTAL
····· TANGENTIAL

FIG.11C
EXAMPLE 3
ω=21.4°

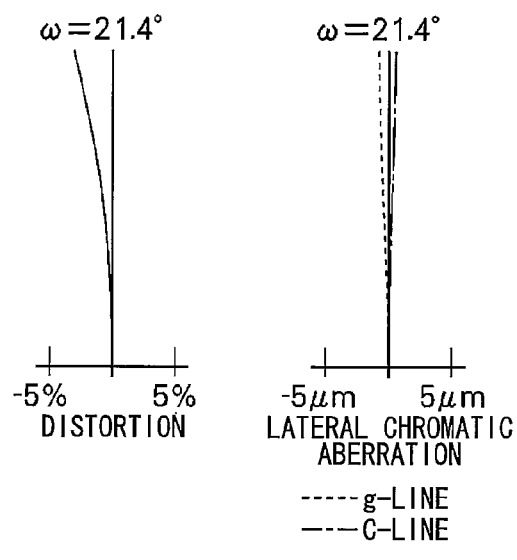

-5%    5%
DISTORTION

FIG.11D
EXAMPLE 3
ω=21.4°

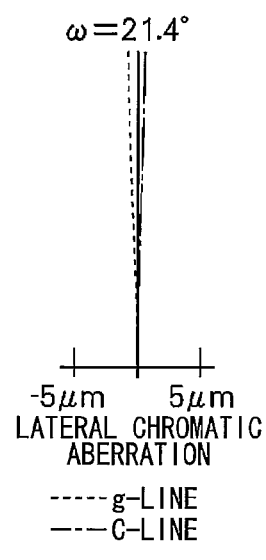

-5μm    5μm
LATERAL CHROMATIC
ABERRATION
----- g-LINE
——— C-LINE

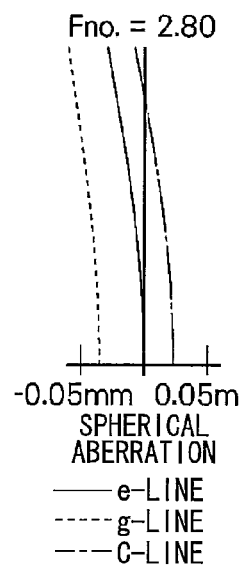

FIG.12A
EXAMPLE 4
Fno. = 2.80

-0.05mm  0.05mm
SPHERICAL
ABERRATION
——— e-LINE
----- g-LINE
——— C-LINE

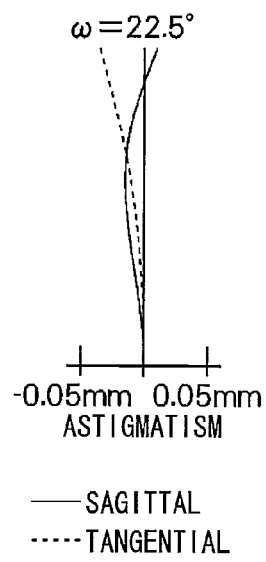

FIG.12B
EXAMPLE 4
ω=22.5°

-0.05mm  0.05mm
ASTIGMATISM
——— SAGITTAL
····· TANGENTIAL

FIG.12C
EXAMPLE 4
ω=22.5°

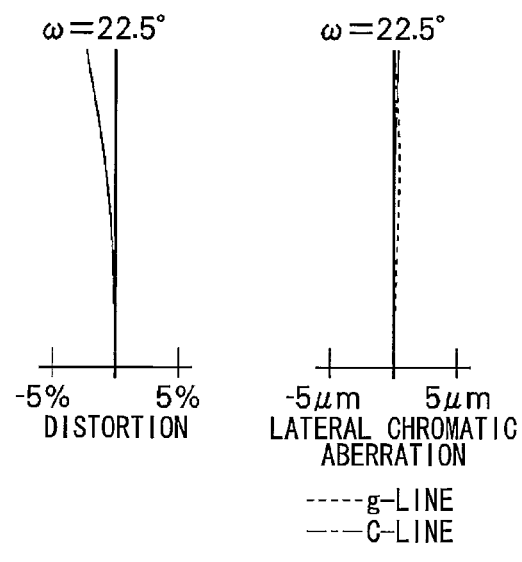

-5%    5%
DISTORTION

FIG.12D
EXAMPLE 4
ω=22.5°

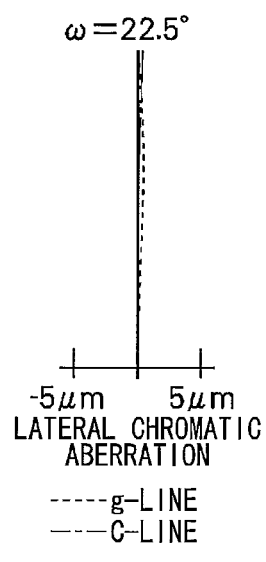

-5μm    5μm
LATERAL CHROMATIC
ABERRATION
----- g-LINE
——— C-LINE

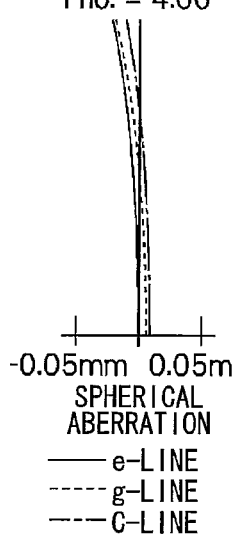

FIG.13A
EXAMPLE 5
Fno. = 4.00

-0.05mm   0.05mm
SPHERICAL
ABERRATION
—— e-LINE
----- g-LINE
--- C-LINE

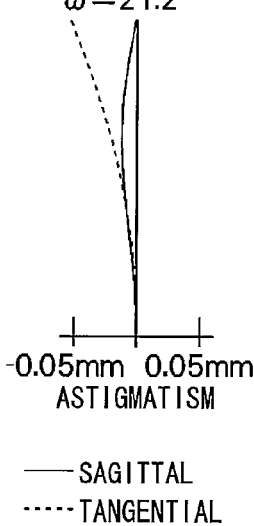

FIG.13B
EXAMPLE 5
ω=21.2°

-0.05mm   0.05mm
ASTIGMATISM

—— SAGITTAL
····· TANGENTIAL

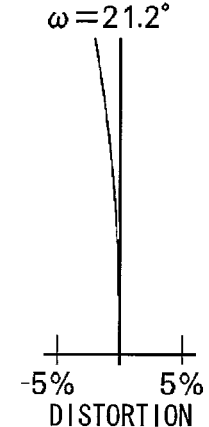

FIG.13C
EXAMPLE 5
ω=21.2°

-5%   5%
DISTORTION

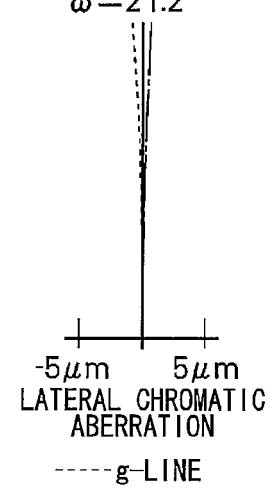

FIG.13D
EXAMPLE 5
ω=21.2°

-5μm   5μm
LATERAL CHROMATIC
ABERRATION
----- g-LINE
--- C-LINE

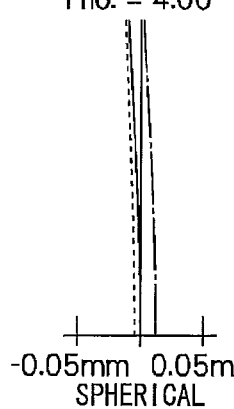

FIG.14A
EXAMPLE 6
Fno. = 4.00

-0.05mm   0.05mm
SPHERICAL
ABERRATION
—— e-LINE
----- g-LINE
--- C-LINE

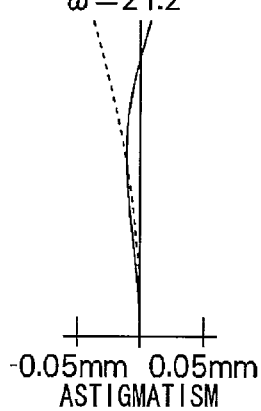

FIG.14B
EXAMPLE 6
ω=21.2°

-0.05mm   0.05mm
ASTIGMATISM

—— SAGITTAL
····· TANGENTIAL

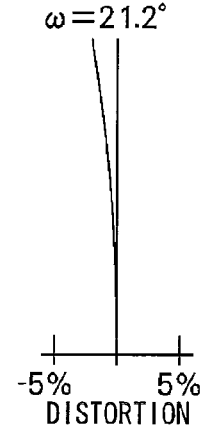

FIG.14C
EXAMPLE 6
ω=21.2°

-5%   5%
DISTORTION

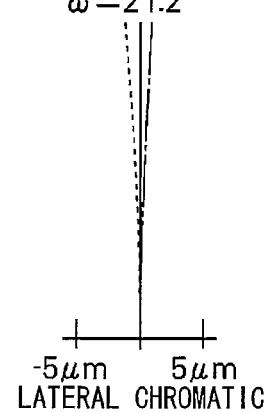

FIG.14D
EXAMPLE 6
ω=21.2°

-5μm   5μm
LATERAL CHROMATIC
ABERRATION
----- g-LINE
--- C-LINE

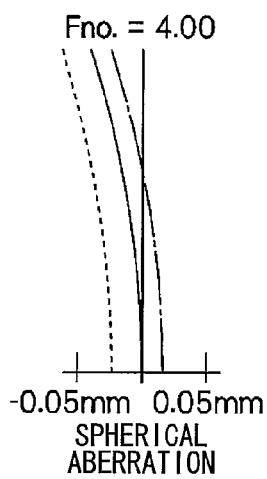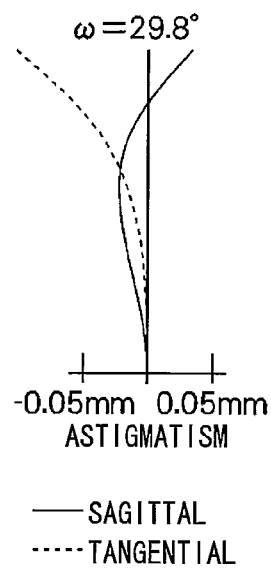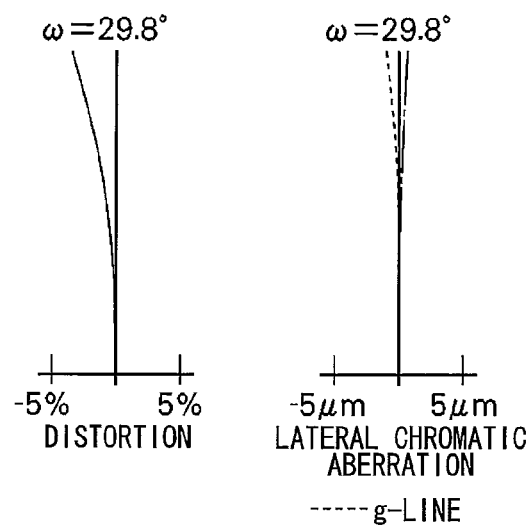
FIG.15A EXAMPLE 7 — Fno. = 4.00 — SPHERICAL ABERRATION — e-LINE, g-LINE, C-LINE
FIG.15B EXAMPLE 7 — ω=29.8° — ASTIGMATISM — SAGITTAL, TANGENTIAL
FIG.15C EXAMPLE 7 — ω=29.8° — DISTORTION
FIG.15D EXAMPLE 7 — ω=29.8° — LATERAL CHROMATIC ABERRATION — g-LINE, C-LINE

IMAGING LENS AND IMAGING APPARATUS USING IMAGING LENS

CROSS-REFERENCE TO RELATED APPLICATIONS

This application is based upon and claims the benefit of priority from the Japanese Patent Application No. 2008-276247 filed on Oct. 28, 2008; the entire contents of which are incorporated herein by reference.

BACKGROUND OF THE INVENTION

1. Field of the Invention

The present invention relates to an imaging lens that captures the image of an object and an imaging apparatus using the imaging lens.

2. Description of the Related Art

An in-vehicle imaging apparatus has been proposed which monitors the front of a vehicle. The imaging apparatus is provided in the vehicle to monitor the deviation of the vehicle from its lane or to monitor traffic signs while the vehicle is traveling. Generally, an imaging lens having a small size and a long back focal length has been used as an in-vehicle imaging lens.

For example, a structure has been proposed in which a cemented lens or a plastic aspheric lens is used as an imaging lens having a small size and a long back focal length (see Japanese Patent Nos. 3254239, 3478643 (U.S. Pat. No. 5,682, 269), 3723637, and 3964533).

Japanese Patent Nos. 3254239, 3478643 (U.S. Pat. No. 5,682,269), 3723637, and 3964533 disclose imaging lenses using cemented lenses. Japanese Patent No. 3254239 discloses an imaging lens that has a large number of lenses including an aspheric lens having a relatively small angle of view. Japanese Patent No. 3478643 (U.S. Pat. No. 5,682,269) discloses an imaging lens using a large number of meniscus lenses. Japanese Patent No. 3723637 discloses an imaging lens having a total length greater than the focal length. Japanese Patent No. 3964533 discloses an imaging lens that has a relatively high F number (Fno=4) and a small angle of view and does not correspond to an increase in diameter.

However, the in-vehicle imaging lens, for example, is provided in the vehicle in severe environments, such as a low-temperature environment of 0° C. or less in a cold region and a high-temperature and high-humidity environment in a tropical region (for example, a temperature of 80° C. and a humidity of 80%). Therefore, a cement of the cemented lens or a plastic lens forming the imaging lens is likely to be transformed or deformed, which may cause deterioration of the optical performance of the imaging lens, for example, a reduction in resolution. In addition, the optical performance of the imaging lens may be lowered due to a variation in the shape or refractive index of the imaging lens caused by a change in the temperature of the imaging lens while capturing the image of an object.

Therefore, it is necessary to prevent the optical performance of the imaging lens from being lowered due to the transformation or deformation of each lens, or the variation in the refractive index of each lens when the imaging lens is provided in a severe environment.

The problem of the deterioration of the optical performance of the imaging lens is not limited to the in-vehicle imaging lens, but it also arises in an imaging lens including a plastic lens or a cemented lens.

SUMMARY OF THE INVENTION

The invention has been made in order to solve the above-mentioned problems, and an object of the invention is to provide an imaging lens having a small size, a long back focal length, and high environmental resistance and an imaging apparatus using the imaging lens.

According to an aspect of the invention, an imaging lens includes a first lens group having a positive power, a stop, and a second lens group having a positive or negative power. The first lens group, the stop, and the second lens group are arranged in this order from an object side. The first lens group includes, in order from the object side, first to third lenses. The first lens is a biconcave lens. The second lens has a positive power and includes a convex image-side surface. The third lens has a positive power and includes a convex object-side surface. The second lens group includes, in order the object side, a fourth lens and a fifth lens. The fourth lens has a negative power and includes a concave image-side surface. The fifth lens is a biconvex lens. Each of the first to fifth lenses is a single spherical glass lens.

The image-side surface of the second lens may be a convex surface having an absolute value of a curvature radius smaller than that of a curvature radius of an object-side surface of the second lens, and the object-side surface of the third lens may be a convex surface having an absolute value of a curvature radius smaller than that of a curvature radius of an image-side surface of the third lens.

That is, it is preferable that the absolute value of the curvature radius of the image-side surface of the second lens be smaller than that of the curvature radius of the object-side surface of the second lens and that the absolute value of the curvature radius of the object-side surface of the third lens be smaller than that of the curvature radius of the image-side surface of the third lens.

The imaging lens may satisfy conditional expression 1 given below:

$0.50 < f13/f < 1.1$      [Conditional expression 1]

(where f indicates a focal length of an entire imaging lens system, and f13 indicates a focal length of the first lens group).

It is more preferable that the imaging lens satisfy conditional expression 1' given below:

$0.60 < f13/f < 1.0$.      [Conditional expression 1']

The imaging lens may satisfy conditional expression 2 given below:

$-0.10 < f/f45 < 0.35$      [Conditional expression 2]

(where f indicates a focal length of an entire imaging lens system, and f45 indicates a focal length of the second lens group).

It is more preferable that the imaging lens satisfy conditional expression 2' given below:

$-0.05 < f/f45 < 0.35$.      [Conditional expression 2']

It is most preferable that the imaging lens satisfy conditional expression 2" given below:

$+0.05 < f/f45 < 0.35$.      [Conditional expression 2"]

The imaging lens may satisfy conditional expression 3 given below:

$-0.95 < f4/f5 < -0.70$      [Conditional expression 3]

(where f4 indicates a focal length of the fourth lens, and f5 indicates a focal length of the fifth lens).

It is more preferable that the imaging lens satisfy conditional expression 3' given below:

$-1.0 < f4/f5 < -0.60$.      [Conditional expression 3']

The imaging lens may satisfy conditional expression 4 given below:

vd4<20 [Conditional expression 4]

(where vd4 indicates the Abbe number of the fourth lens at the d-line).

According to the imaging lens and the imaging apparatus using the imaging lens of the above-mentioned aspects, the imaging lens includes, in order from the object side, the first lens group having the positive power, the stop, and the second lens group having the positive or negative power. The first lens group includes, in order from the object side, the first lens, which is the biconcave lens, the second lens that has the positive power and includes the convex image-side surface, and the third lens that has the positive power and includes the convex object-side surface. The second lens group includes, in order from the object side, the fourth lens that has the negative power and includes the concave image-side surface, and the fifth lens, which is the biconvex lens. Each of the first to fifth lenses is a single spherical glass lens. With this structure, it is possible to obtain an imaging lens having a small size, a long back focal length and high environmental resistance.

That is, both the lens closest to the object side in the first lens group and the lens closest to the object side in the second lens group have negative powers. Particularly, the lens closest to the object side in the first lens group is the biconcave lens. Therefore, it is possible to increase the back focal length while reducing the length of the entire imaging lens system.

The back focal length is an air equivalent distance from the lens surface closest to the image side among the lens surfaces of the imaging lens to the image formation surface of the imaging lens.

The cement of the cemented lens or the plastic lens is made of a material, such as a polymer material, having a melting point lower than that of a glass material. The low-melting-point material is more likely to be deformed by the influence of the temperature or humidity than the glass material, and the optical characteristics thereof, such as the refractive index, are also more likely to be changed. In addition, the low-melting-point material is more likely to be transformed than the glass material. Therefore, when the imaging lens is used for a long time, the optical performance of the imaging lens is lowered.

According to the above-mentioned aspects of the invention, the imaging lens is not made of the low-melting-point material, but is made of only the glass member having high environmental resistance. Therefore, it is possible to obtain an imaging lens and an imaging apparatus having high environmental resistance. In addition, since the imaging lens includes only the spherical lenses, it is possible to easily manufacture the imaging lens, as compared to an imaging lens including aspheric lenses. As a result, it is possible to reduce apparatus costs.

When the environmental resistance of the imaging lens is increased, the deterioration of the optical performance of the imaging lens caused by the influence of an environment is reduced. For example, when the environmental resistance of the imaging lens is high, the transformation or deformation of the lens member is reduced, and the deterioration of the optical performance of the imaging lens is reduced even when the imaging lens is used for a long time or it is provided in a low-temperature environment or a high-temperature and high-humidity environment in a short period of time. In addition, when the environmental resistance of the imaging lens is high, the deterioration of the optical performance of the imaging lens is reduced even when the temperature of the imaging lens varies greatly from a room temperature during image capture in a cold region or a tropical region.

BRIEF DESCRIPTION OF THE DRAWINGS

FIG. 2 is a cross-sectional view schematically illustrating the structure of an imaging lens according to Example 1;

FIG. 3 is a cross-sectional view schematically illustrating the structure of an imaging lens according to Example 2;

FIG. 4 is a cross-sectional view schematically illustrating the structure of an imaging lens according to Example 3;

FIG. 5 is a cross-sectional view schematically illustrating the structure of an imaging lens according to Example 4;

FIG. 8 is a cross-sectional view schematically illustrating the structure of an imaging lens according to Example 7;

FIGS. 9A to 9D are diagrams illustrating all aberrations of the imaging lens according to Example 1, in which FIG. 9A shows spherical aberration, FIG. 9B shows astigmatism, FIG. 9C shows distortion, and FIG. 9D shows lateral chromatic aberration;

FIGS. 10A to 10D are diagrams illustrating all aberrations of the imaging lens according to Example 2, in which FIG. 10A shows spherical aberration, FIG. 10B shows astigmatism, FIG. 10C shows distortion, and FIG. 10D shows lateral chromatic aberration;

FIGS. 11A to 11D are diagrams illustrating all aberrations of the imaging lens according to Example 3, in which FIG. 11A shows spherical aberration, FIG. 11B shows astigmatism, FIG. 11C shows distortion, and FIG. 11D shows lateral chromatic aberration;

FIGS. 12A to 12D are diagrams illustrating all aberrations of the imaging lens according to Example 4, in which FIG. 12A shows spherical aberration, FIG. 12B shows astigmatism, FIG. 12C shows distortion, and FIG. 12D shows lateral chromatic aberration;

FIGS. 13A to 13D are diagrams illustrating all aberrations of the imaging lens according to Example 5, in which FIG. 13A shows spherical aberration, FIG. 13B shows astigmatism, FIG. 13C shows distortion, and FIG. 13D shows lateral chromatic aberration;

FIG. 14A to 14D are diagrams illustrating all aberrations of the imaging lens according to Example 6, in which FIG. 14A shows spherical aberration, FIG. 14B shows astigmatism, FIG. 14C shows distortion, and FIG. 14D shows lateral chromatic aberration;

FIGS. 15A to 15D are diagram illustrating all aberrations of the imaging lens according to Example 7, in which FIG. 15A shows spherical aberration, FIG. 15B shows astigmatism, FIG. 15C shows distortion, and FIG. 15D shows lateral chromatic aberration.

DESCRIPTION OF THE PREFERRED EMBODIMENTS

Hereinafter, an imaging lens and an imaging apparatus using the imaging lens according to exemplary embodiments of the invention will be described in detail with reference to the accompanying drawings.

Figure 1:
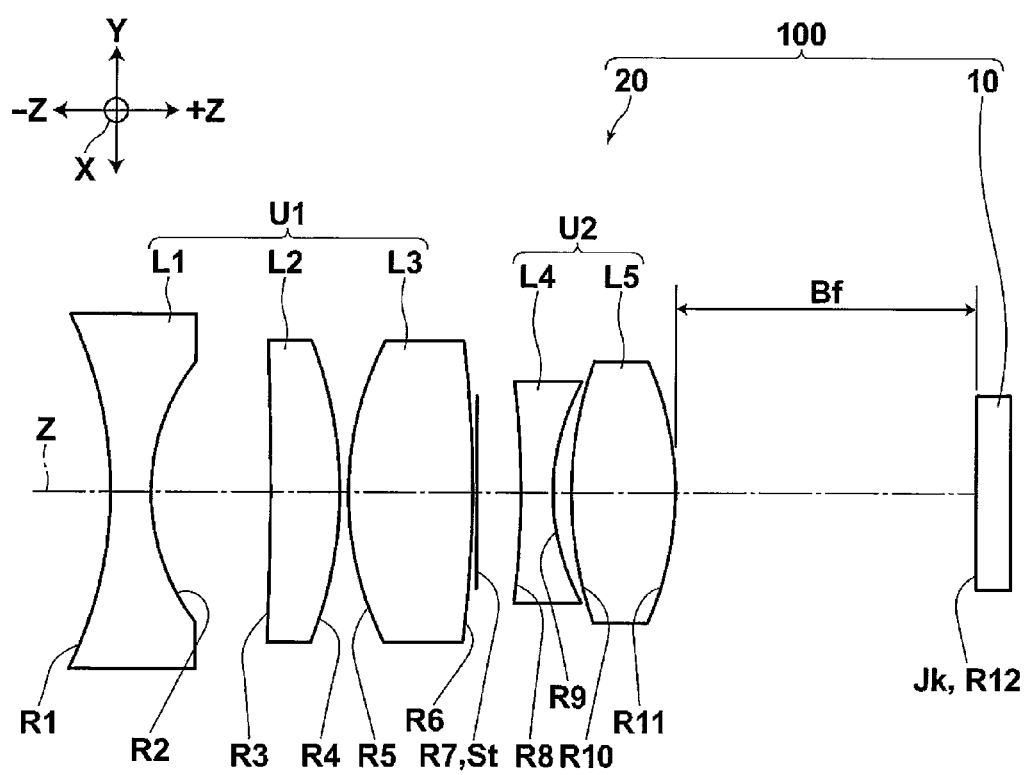
FIG. 1 is a diagram schematically illustrating the structure of an imaging lens according to an embodiment of the invention.
Figure 6:
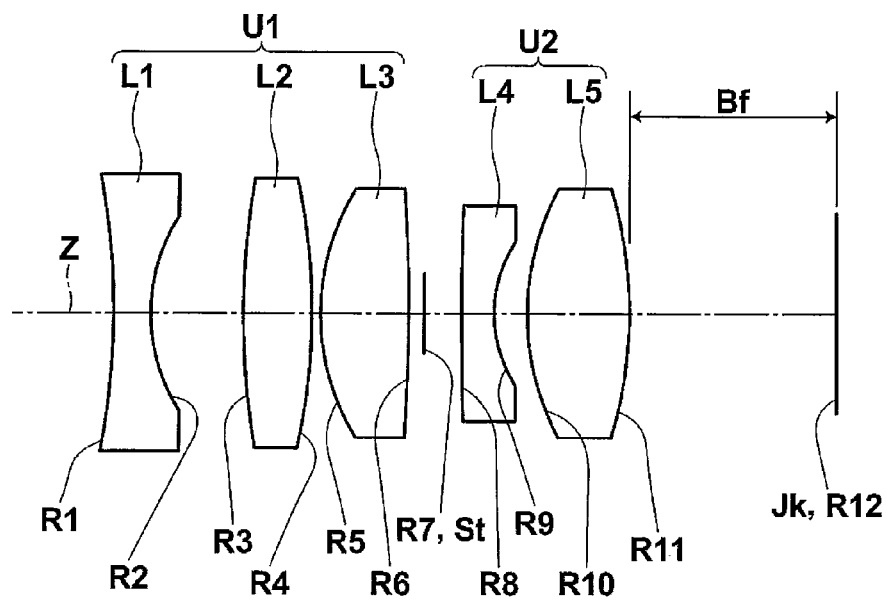
FIG. 6 is a cross-sectional view schematically illustrating the structure of an imaging lens according to Example 5.
Figure 7:
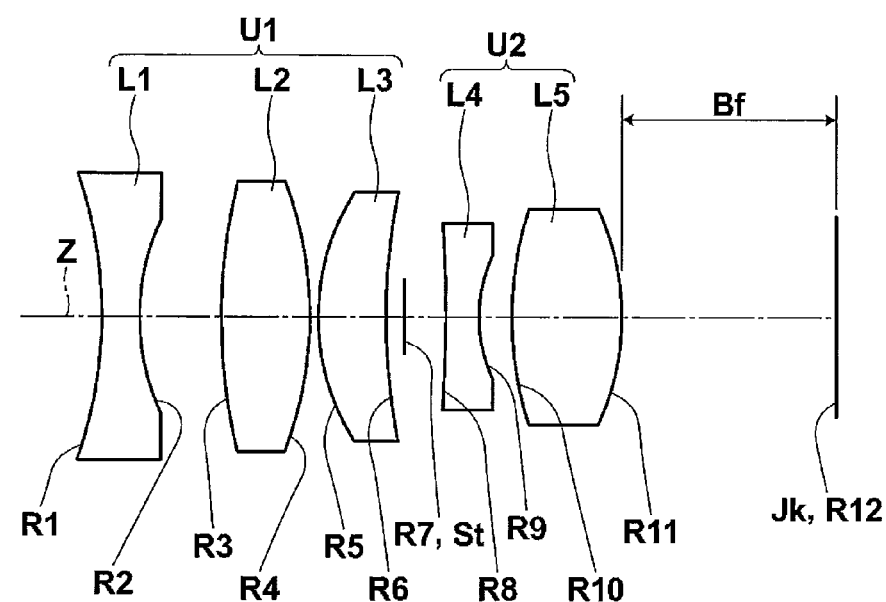
FIG. 7 is a cross-sectional view schematically illustrating the structure of an imaging lens according to Example 6.

FIG. 1 is a cross-sectional view schematically illustrating the structure of an imaging apparatus using an imaging lens according to an embodiment of the invention.

An imaging lens 20 shown in FIG. 1 is mainly used for an in-vehicle imaging apparatus that captures a situation on the front side of a vehicle, and focuses the image of an object on a light receiving surface Jk of an imaging device 10, such as a CCD or a CMOS. The imaging device 10 converts an optical image formed by the imaging lens 20 into an electric signal to obtain an image signal indicating the optical image.

The imaging lens 20 has an F number of 2.0 to 4.0 and a total angle of view of about 40° to 60°. The imaging lens 20 has a small size and a long back focal length and effectively corrects all aberrations.

<Basic Structure, Operation, and Effect of Imaging Lens>

First, the basic structure of the imaging lens 20 will be described.

The imaging lens 20 includes, in order from an object side (the side of an arrow −Z in FIG. 1) along an optical axis Z1, a first lens group U1 having a positive power, an aperture diaphragm, and a second lens group U2 having a positive or negative power.

The first lens group U1 includes a first lens L1, which is a biconcave lens, a second lens L2 that has a positive power and includes a convex surface on the image side (the side of an arrow +Z in FIG. 1), and a third lens L3 that has a positive power and includes a convex surface on the object side (the side of the arrow −Z in FIG. 1). The first to third lenses are arranged in this order from the object side.

The second lens group U2 includes a fourth lens L4 that has a negative power and includes a concave image-side surface and a fifth lens L5, which is a biconvex lens. The fourth and fifth lenses are arranged in this order from the object side.

Each of the first to fifth lenses L1 to L5 is a single spherical lens made of a glass material.

That is, each of the lenses of the imaging lens 20 is a single spherical glass lens, but is not a cemented lens.

A light receiving surface Jk of the imaging device 10 is provided as an imaging surface R12 on which the image of an object is focused by the imaging lens 20.

In FIG. 1, reference numerals R1 to R12 denote the following components.

That is, R1 and R2 indicate the object-side surface and the image-side surface of the first lens L1, respectively, and R3 and R4 indicate the object-side surface and the image-side surface of the second lens L2, respectively. R5 and R6 indicate the object-side surface and the image-side surface of the third lens L3, respectively, and R7 indicates an aperture of the aperture diaphragm St. R8 and R9 indicate the object-side surface and the image-side surface of the fourth lens L4, respectively, and R10 and R11 indicate the object-side surface and the image-side surface of the fifth lens L5, respectively. R12 indicates the imaging surface of the imaging lens 20, which is the light receiving surface Jk of the imaging device 10, as described above.

According to the basic structure of the imaging lens 20, it is possible to obtain an imaging lens having a small size, a long back focal length, and high environmental resistance.

The back focal length (which is represented by Bf in the drawings) is an air equivalent distance from the image-side surface R11 of the fifth lens L5 to the imaging surface R12.

<Structure Further Limiting Basic Structure of Imaging Lens and Operation and Effect Thereof>

Next, components further limiting the basic structure of the imaging lens 20 and the operation and effect thereof will be described. The components further limiting the basic structure of the imaging lens according to this embodiment of the invention are not necessarily required.

<<Structure for Limiting the Basic Structure Using Conditional Expressions and Operation and Effect Thereof>>

Hereinafter, a structure for limiting the basic structure and the operation and effect thereof will be described.

The absolute value of the curvature radius of the convex image-side surface R4 of the second lens L2 is smaller than that of the curvature radius of the object-side surface R3 of the second lens L2, and the absolute value of the curvature radius of the convex object-side surface R5 of the third lens L3 is smaller than that of the curvature radius of the image-side surface R7 of the third lens L3. That is, in the second lens L2 and the third lens L3, the lens surfaces having a small absolute value of the curvature radius (the lens surface R4 and the lens surface R5) face each other. In this way, it is possible to correct comatic aberration while preventing the occurrence of longitudinal chromatic aberration and lateral chromatic aberration.

Next, Conditional expressions 1 to 4 for limiting the basic structure of the imaging lens and the operation and effect thereof will be described.

The imaging lens according to this embodiment may satisfy only one of a plurality of structures limiting the basic structure, or combinations of two or more of the plurality of structures limiting the basic structure.

The meaning of each of the parameters represented by symbols in Conditional expressions 1 to 4 will be described below: f indicates the focal length of the entire imaging lens system, that is, the composite focal length of the first lens L1 to the fifth lens L5; f4 indicates the focal length of the fourth lens; f5 indicates the focal length of the fifth lens; f13 indicates the focal length of the first lens group U1 (the composite focal length of the first lens to the third lens); f45 indicates the focal length of the second lens group U2 (the composite focal length of the fourth lens and the fifth lens); and vd4 indicates the Abbe number of the fourth lens at the d-line.

The following Conditional expression 1 relates to longitudinal chromatic aberration, lateral chromatic aberration, and spherical aberration:

$$0.50 < f13/f < 1.1. \qquad \text{[Conditional expression 1]}$$

When the lens system is configured so as to satisfy Conditional expression 1, it is possible to effectively correct longitudinal chromatic aberration, lateral chromatic aberration, and spherical aberration.

However, when the lens system is configured such that the value of f13/f is greater than the upper limit of Conditional expression 1, that is, the value of f13/f is equal to or greater than 1.1, it is difficult to correct longitudinal chromatic aberration and lateral chromatic aberration at the same time.

On the other hand, when the lens system is configured such that the value of f13/f is less than the lower limit of Conditional expression 1, that is, the value of f13/f is equal to or less than 0.50, it is difficult to correct spherical aberration.

It is more preferable that the value of f13/f satisfy Conditional expression 1' given below:

$$0.60 < f13/f < 1.0. \qquad \text{[Conditional expression 1']}$$

The following Conditional expression 2 relates to field curvature or a back focal length:

$$-0.10 < f/f45 < 0.35. \qquad \text{[Conditional expression 2]}$$

When the lens system is configured so as to satisfy Conditional expression 2, it is possible to ensure a long back focal length without increasing the total length of the lens system and prevent field curvature.

However, when the lens system is configured such that the value of f/f45 is greater than the upper limit of Conditional expression 2, that is, the value of f/f45 is equal to or greater than 0.35, it is difficult to correct field curvature.

On the other hand, when the lens system is configured such that the value of f/f45 is less than the lower limit of Conditional expression 2, that is, the value of f/f45 is equal to or less than −0.10, it is difficult to ensure a long back focal length without increasing the total length of the lens system.

It is more preferable that the value of f/f45 satisfy Conditional expression 2' given below:

$$-0.05 < f/f45 < 0.35. \quad \text{[Conditional expression 2']}$$

It is most preferable that the value of f/f45 satisfy Conditional expression 2" given below:

$$+0.05 < f/f45 < 0.35. \quad \text{[Conditional expression 2'']}$$

The following Conditional expression 3 relates to lateral chromatic aberration, spherical aberration, and field curvature:

$$-0.95 < f4/f5 < -0.70. \quad \text{[Conditional expression 3]}$$

When the lens system is configured so as to satisfy Conditional expression 3, it is possible to effectively correct lateral chromatic aberration, spherical aberration, and field curvature.

However, when the lens system is configured such that the value of f4/f5 is greater than the upper limit of Conditional expression 3, that is, the value of f4/f5 is equal to or greater than −0.70, it is difficult to correct spherical aberration and field curvature at the same time.

On the other hand, when the lens system is configured such that the value of f4/f5 is less than the lower limit of Conditional expression 3, that is, the value of f4/f5 is equal to or smaller than −0.70, it is difficult to correct lateral chromatic aberration.

The following Conditional expression 4 relates to longitudinal chromatic aberration and lateral chromatic aberration:

$$vd4 < 20. \quad \text{[Conditional expression 4]}$$

When the lens system is configured so as to satisfy Conditional expression 4, it is possible to effectively correct longitudinal chromatic aberration and lateral chromatic aberration.

However, when the lens system is configured such that the value of vd4 is greater than the upper limit of Conditional expression 4, that is, the Abbe number vd4 of a material forming the fourth lens L4 at the d-line is equal to or greater than 20, it is difficult to correct longitudinal chromatic aberration and lateral chromatic aberration.

As described above, according to this embodiment of the invention, it is possible to obtain an imaging lens having a small size, a long back focal length, and high environmental resistance.

Detailed Examples

Next, numerical data of the imaging lenses according to Examples 1 to 7 of the invention will be described with reference to FIGS. 2 to 15 and Tables 1 to 7. FIGS. 2 to 8 are cross-sectional views schematically illustrating the structures of the imaging lenses according to Examples 1 to 7. In FIGS. 2 to 8, the same reference numerals as those in FIG. 1 denote the corresponding components.

The following Tables 1 to 7 shows basic data of the imaging lenses according to Examples 1 to 7. In each of the tables, an upper part shows lens data of the imaging lenses (which is represented by (a) in the drawings) and a lower part shows the brief specifications of the imaging lenses (which is represented by (b) in the drawings).

TABLE 1

EXAMPLE 1

(a) LENS DATA

| SURFACE NUMBER | Ri | di | Ndj | vdj |
|---|---|---|---|---|
| 1 | −10.06 | 1.00 | 1.51823 | 58.9 |
| 2 | 5.320 | 2.96 | | |
| 3 | −90.88 | 1.71 | 1.83481 | 42.7 |
| 4 | −10.16 | 0.20 | | |
| 5 | 8.204 | 3.09 | 1.83481 | 42.7 |
| 6 | −30.64 | 0.10 | | |
| 7(St) | | 1.10 | | |
| 8 | −22.23 | 0.79 | 1.92286 | 18.9 |
| 9 | 5.557 | 0.47 | | |
| 10 | 9.699 | 2.59 | 1.83481 | 42.7 |
| 11 | −8.053 | 7.43 | | |
| 12 | ∞ | | | |

(b) BRIEF SPECIFICATIONS

| | |
|---|---|
| f | 6.53 |
| Fno | 2.00 |
| 2ω | 42.7 |
| f13 | 5.71 |
| f45 | 55.6 |
| f4 | −4.75 |
| f5 | 5.65 |
| f13/f | 0.875 |
| f/f45 | 0.117 |
| f4/f5 | −0.842 |
| vd4 | 18.9 |

TABLE 2

EXAMPLE 2

(a) LENS DATA

| SURFACE NUMBER | Ri | di | Ndj | vdj |
|---|---|---|---|---|
| 1 | −11.04 | 1.00 | 1.65412 | 39.7 |
| 2 | 6.594 | 2.89 | | |
| 3 | 32.90 | 1.90 | 1.83481 | 42.7 |
| 4 | −11.75 | 0.20 | | |
| 5 | 7.007 | 3.78 | 1.83481 | 42.7 |
| 6 | 44.49 | 0.15 | | |
| 7(St) | | 0.92 | | |
| 8 | 25.86 | 0.80 | 1.92286 | 18.9 |
| 9 | 3.943 | 0.62 | | |
| 10 | 6.072 | 2.61 | 1.83481 | 42.7 |
| 11 | −16.11 | 5.58 | | |
| 12 | ∞ | | | |

(b) BRIEF SPECIFICATIONS

| | |
|---|---|
| f | 6.54 |
| Fno | 2.00 |
| 2ω | 42.7 |
| f13 | 6.12 |
| f45 | 57.10 |
| f4 | −5.13 |
| f5 | 5.58 |
| f13/f | 0.936 |
| f/f45 | 0.115 |
| f4/f5 | −0.919 |
| vd4 | 18.9 |

TABLE 3

EXAMPLE 3

(a) LENS DATA

| SURFACE NUMBER | Ri | di | Ndj | vdj |
|---|---|---|---|---|
| 1 | −8.979 | 1.00 | 1.62004 | 36.3 |
| 2 | 7.038 | 2.41 | | |
| 3 | 28.58 | 2.04 | 1.88300 | 40.8 |
| 4 | −12.35 | 0.20 | | |
| 5 | 6.886 | 3.87 | 1.83481 | 42.7 |
| 6 | 49.94 | 0.14 | | |
| 7(St) | | 0.90 | | |
| 8 | 19.82 | 0.97 | 1.92286 | 18.9 |
| 9 | 3.592 | 0.48 | | |
| 10 | 5.115 | 2.68 | 1.88300 | 40.8 |
| 11 | −39.01 | 4.63 | | |
| 12 | ∞ | | | |

(b) BRIEF SPECIFICATIONS

| | |
|---|---|
| f | 6.54 |
| Fno | 2.00 |
| 2ω | 42.7 |
| f13 | 6.10 |
| f45 | 167.2 |
| f4 | −4.90 |
| f5 | 5.27 |
| f13/f | 0.932 |
| f/f45 | 0.039 |
| f4/f5 | −0.929 |
| vd4 | 18.9 |

TABLE 4

EXAMPLE 4

(a) LENS DATA

| SURFACE NUMBER | Ri | di | Ndj | vdj |
|---|---|---|---|---|
| 1 | −10.31 | 0.93 | 1.58144 | 40.7 |
| 2 | 6.168 | 2.11 | | |
| 3 | 33.55 | 2.18 | 1.88300 | 40.8 |
| 4 | −8.840 | 0.20 | | |
| 5 | 4.940 | 2.35 | 1.88300 | 40.8 |
| 6 | 10.71 | 0.17 | | |
| 7(St) | | 0.96 | | |
| 8 | 20.01 | 1.00 | 2.14352 | 17.8 |
| 9 | 3.281 | 0.60 | | |
| 10 | 6.086 | 2.97 | 1.88300 | 40.8 |
| 11 | −8.518 | 3.73 | | |
| 12 | ∞ | | | |

(b) BRIEF SPECIFICATIONS

| | |
|---|---|
| f | 6.08 |
| Fno | 2.80 |
| 2ω | 44.9 |
| f13 | 4.88 |
| f45 | 46.7 |
| f4 | −3.55 |
| f5 | 4.44 |
| f13/f | 0.802 |
| f/f45 | 0.130 |
| f4/f5 | −0.798 |
| vd4 | 17.8 |

TABLE 5

EXAMPLE 5

(a) LENS DATA

| SURFACE NUMBER | Ri | di | Ndj | vdj |
|---|---|---|---|---|
| 1 | −17.87 | 0.90 | 1.58144 | 40.7 |
| 2 | 4.411 | 2.22 | | |
| 3 | 19.01 | 1.67 | 1.83481 | 42.7 |
| 4 | −14.90 | 0.20 | | |
| 5 | 5.633 | 2.14 | 1.83481 | 42.7 |
| 6 | −46.52 | 0.39 | | |
| 7(St) | | 0.89 | | |
| 8 | 86.95 | 0.80 | 1.92286 | 18.9 |
| 9 | 3.171 | 0.80 | | |
| 10 | 6.346 | 2.46 | 1.83481 | 42.7 |
| 11 | −10.47 | 4.99 | | |
| 12 | ∞ | | | |

(b) BRIEF SPECIFICATIONS

| | |
|---|---|
| f | 6.44 |
| Fno | 4.00 |
| 2ω | 42.4 |
| f13 | 4.53 |
| f45 | −113.2 |
| f4 | −3.58 |
| f5 | 5.07 |
| f13/f | 0.703 |
| f/f45 | −0.057 |
| f4/f5 | −0.707 |
| vd4 | 18.9 |

TABLE 6

EXAMPLE 6

(a) LENS DATA

| SURFACE NUMBER | Ri | di | Ndj | vdj |
|---|---|---|---|---|
| 1 | −10.38 | 0.90 | 1.58144 | 40.7 |
| 2 | 5.545 | 1.97 | | |
| 3 | 13.91 | 2.13 | 1.83481 | 42.7 |
| 4 | −9.145 | 0.20 | | |
| 5 | 5.531 | 1.64 | 1.83481 | 42.7 |
| 6 | 15.41 | 0.44 | | |
| 7(St) | | 1.00 | | |
| 8 | −33.71 | 0.80 | 1.92286 | 18.9 |
| 9 | 3.598 | 0.80 | | |
| 10 | 8.436 | 2.64 | 1.83481 | 42.7 |
| 11 | −6.219 | 5.15 | | |
| 12 | ∞ | | | |

(b) BRIEF SPECIFICATIONS

| | |
|---|---|
| f | 6.44 |
| Fno | 4.00 |
| 2ω | 42.4 |
| f13 | 4.95 |
| f45 | 29.2 |
| f4 | −3.49 |
| f5 | 4.67 |
| f13/f | 0.769 |
| f/f45 | 0.221 |
| f4/f5 | −0.746 |
| vd4 | 18.9 |

TABLE 7

EXAMPLE 7

(a) LENS DATA

| SURFACE NUMBER | Ri | di | Ndj | vdj |
|---|---|---|---|---|
| 1 | −12.48 | 2.00 | 1.55030 | 46.3 |
| 2 | 4.797 | 2.22 | | |
| 3 | 48.00 | 2.20 | 1.83849 | 42.3 |
| 4 | −7.324 | 2.00 | | |
| 5 | 3.869 | 1.50 | 1.82851 | 43.4 |
| 6 | 11.21 | 0.43 | | |
| 7(St) | | 0.29 | | |
| 8 | 20.15 | 0.87 | 1.92286 | 18.9 |
| 9 | 2.547 | 0.80 | | |
| 10 | 7.659 | 2.35 | 1.81951 | 44.4 |
| 11 | −4.894 | 3.28 | | |
| 12 | ∞ | | | |

(b) BRIEF SPECIFICATIONS

| | |
|---|---|
| f | 4.50 |
| Fno | 4.00 |
| 2ω | 59.7 |
| f13 | 3.63 |
| f45 | 15.1 |
| f4 | −3.24 |
| f5 | 3.98 |
| f13/f | 0.807 |
| f/f45 | 0.297 |
| f4/f5 | −0.813 |
| vd4 | 18.9 |

In the upper part in the lens data shown in Tables 1 to 7, the surface number of an optical member, such as a lens, from the object side is represented by an i-th (i=1 to 12) surface number, and the surface number is sequentially increased toward the image side. In addition, the lens data includes the surface number (i=7) of the aperture diaphragm St and the surface number (i=12) of the imaging surface.

Ri indicates the curvature radius of the i-th (i=1, 2, 3, . . . ) surface, and Di indicates the surface spacing between the i-th (i=1, 2, 3, . . . ) surface and an (i+1)-th surface on the optical axis Z1. In the lens data, Ri corresponds to Ri (i=1, 2, 3, . . . ) indicating the lens surface in FIG. 1.

In addition, in the lens data, Ndj indicates the refractive index of a j-th (j=1, 2, 3, . . . ) optical component from the object side at the d-line (wavelength: 587.6 nm). The number of the optical component is sequentially increased toward the image side. In addition, vdj indicates the Abbe number of the j-th optical component at the d-line.

The units of the curvature radius and the surface spacing are millimeters (mm). When the lens surface is convex toward the object side, the curvature radius thereof has a positive value. When the lens surface is convex toward the image side, the curvature radius thereof has a negative value.

The symbols of each item in the brief specifications shown in the lower part of each of Tables 1 to 7 correspond to the following content. Some of the following symbols have already been described above.

That is, the brief specifications of the following items are shown in Tables 1 to 7: f indicates the focal length of the entire imaging lens system (the composite focal length of the first lens to the fifth lens); Fno indicates the F number; 2ω indicates a total angle of view; f13 indicates the focal length of the first lens group U1 including the first lens, the second lens, and the third lens; f45 indicates the focal length of the second lens group U2 including the fourth lens and the fifth lens; f4 indicates the focal length of the fourth lens; f5 indicates the focal length of the fifth lens; and vd4 indicates the Abbe number of the fourth lens at the d-line.

FIGS. 9 to 15 are diagrams illustrating all aberration of the imaging lenses according to Examples 1 to 7. FIGS. 9 to 15 show the aberrations of the imaging lenses according to Examples 1 to 7 at the e-line (wavelength: 546.1 nm), the g-line (wavelength: 435.8 nm), and the C-line (wavelength: 656.3 nm).

The distortion diagram shows the amount of deviation from an ideal image height f×tan θ when the focal length of the entire lens system is f and an angle of view is θ (a variable, $0 \leq \theta \leq \omega$).

As can be seen from the basic data of Examples 1 to 7 and the diagrams illustrating all aberrations, according to the imaging lens of the invention, it is possible to optimize the shape and material of each of the five lenses. Therefore, it is possible to obtain an imaging lens having a small size, a long back focal length, and high environmental resistance.

Although the embodiment and the examples of the invention have been described above, the invention is not limited to the embodiment and the examples, but various modifications and changes of the invention can be made. For example, the curvature radius, surface spacing, and refractive index of each lens component are not limited to the values shown in the drawings, but each lens component may have other values.

Figure 16:
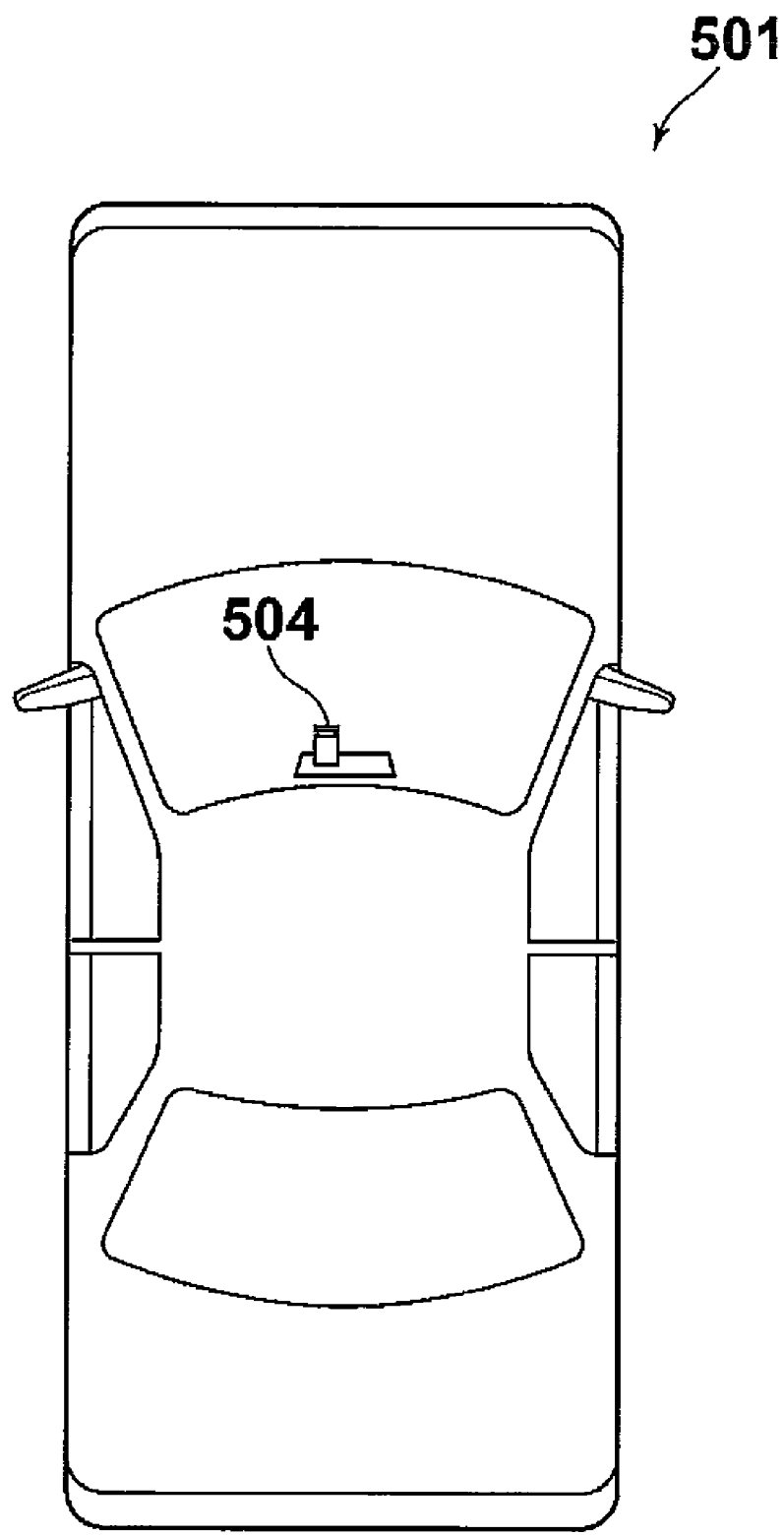
FIG. 16 is a diagram illustrating a vehicle provided with an in-vehicle camera, which is an imaging apparatus using the imaging lens according to the invention.

FIG. 16 is a diagram illustrating a vehicle provided with an in-vehicle camera, which is an example of an imaging apparatus according to the invention that includes the imaging lens according to the invention and an imaging device converting the optical image formed by the imaging lens into an electric signal.

As shown in FIG. 16, an in-vehicle camera 504 using the imaging lens according to the invention is mounted to the rear surface of a room mirror of a vehicle 501 and captures the front view of the vehicle 501. When the vehicle 501 is traveling, the in-vehicle camera 504 captures the front view to monitor the deviation of the vehicle 501 from its lane, traffic signs, or whether there is an obstacle in the course.

What is claimed is:
1. An imaging lens comprising:
a first lens group having a positive power;
a stop; and
a second lens group having a positive or negative power,
wherein the first lens group, the stop, and the second lens group are arranged in this order from an object side,
the first lens group includes, in order from the object side,
  a first lens, which is a biconcave lens,
  a second lens that has a positive power and includes a convex image-side surface, and
  a third lens that has a positive power and includes a convex object-side surface,
the second lens group includes, in order from the object side,
  a fourth lens that has a negative power and includes a concave image-side surface, and
  a fifth lens, which is a biconvex lens, and
each of the first to fifth lenses is a single spherical glass lens.
2. The imaging lens according to claim 1,
wherein an absolute value of a curvature radius of the image-side surface of the second lens is smaller than that of a curvature radius of an object-side surface of the second lens, and
an absolute value of a curvature radius of the object-side surface of the third lens is smaller than that of a curvature radius of an image-side surface of the third lens.

3. The imaging lens according to claim 1,
wherein the imaging lens satisfies the following conditional expression:

$$0.50 < f13/f < 1.1$$

where f indicates a focal length of an entire imaging lens system, and f13 indicates a focal length of the first lens group.

4. The imaging lens according to claim 1,
wherein the imaging lens satisfies the following conditional expression:

$$-0.10 < f/f45 < 0.35$$

where f indicates a focal length of an entire imaging lens system, and f45 indicates a focal length of the second lens group.

5. The imaging lens according to claim 1,
wherein the imaging lens satisfies the following conditional expression:

$$-0.95 < f4/f5 < -0.70$$

where f4 indicates a focal length of the fourth lens, and f5 indicates a focal length of the fifth lens.

6. The imaging lens according to claim 1,
wherein the imaging lens satisfies the following conditional expression:

$$vd4 < 20$$

where vd4 indicates the Abbe number of the fourth lens at the d-line.

7. An imaging apparatus comprising:
the imaging lens according to claim 1; and
an imaging device that converts an optical image formed by the imaging lens into an electric signal.

* * * * *